(12) United States Patent
Jenkins

(10) Patent No.: US 10,349,979 B2
(45) Date of Patent: Jul. 16, 2019

(54) PROCEDURE FOR REMOVING A FOOD MASS LODGED IN THE ESOPHAGUS

(71) Applicant: Alma F. Jenkins, Goldsboro, NC (US)

(72) Inventor: Alma F. Jenkins, Goldsboro, NC (US)

( * ) Notice: Subject to any disclaimer, the term of this patent is extended or adjusted under 35 U.S.C. 154(b) by 182 days.

(21) Appl. No.: 15/671,602

(22) Filed: Aug. 8, 2017

(65) Prior Publication Data

US 2019/0046238 A1     Feb. 14, 2019

(51) Int. Cl.
| | | |
|---|---|---|
| *A61B 17/52* | (2006.01) | |
| *A61B 17/00* | (2006.01) | |
| *A61B 17/22* | (2006.01) | |
| *A61B 17/29* | (2006.01) | |
| *A61B 17/28* | (2006.01) | |
| *A61B 17/24* | (2006.01) | |

(52) U.S. Cl.
CPC ........ *A61B 17/52* (2013.01); *A61B 17/00234* (2013.01); *A61B 17/22031* (2013.01); *A61B 17/24* (2013.01); *A61B 17/28* (2013.01); *A61B 17/29* (2013.01); *A61B 2017/00287* (2013.01); *A61B 2017/00358* (2013.01); *A61B 2017/00876* (2013.01)

(58) Field of Classification Search
CPC ......... A61B 17/50; A61B 17/52; A61B 17/24; A61B 17/00234; A61B 17/28; A61B 17/2804; A61B 17/282; A61B 17/29; A61B 17/22031; A61B 2017/00287; A61B 2017/00292; A61B 2017/2926; A61B 2017/2945; A61B 2017/00358; A61B 2017/00876; A61B 2017/00238

See application file for complete search history.

(56) References Cited

U.S. PATENT DOCUMENTS

| | | | |
|---|---|---|---|
| 2,753,869 A | | 7/1956 | Muffly |
| 4,657,020 A | * | 4/1987 | Lifton ..................... A61B 17/50 606/106 |
| 5,364,404 A | | 11/1994 | Jaffe et al. |
| 5,800,394 A | * | 9/1998 | Yoon ................ A61B 17/00234 600/207 |
| 8,293,213 B2 | * | 10/2012 | Schwartz ................. A61N 2/06 424/178.1 |
| 8,333,695 B2 | * | 12/2012 | Cuschieri ............... A61B 17/02 600/201 |
| 9,549,761 B2 | * | 1/2017 | Green .............. A61B 17/00234 |
| 9,901,245 B2 | * | 2/2018 | Kovarik ........... A61B 17/22031 |
| 2008/0103508 A1 | * | 5/2008 | Karakurum ...... A61B 17/00234 606/127 |
| 2008/0243137 A1 | | 10/2008 | D'Angelo et al. |
| 2012/0221010 A1 | | 8/2012 | DeLuca et al. |
| 2016/0374700 A1 | | 12/2016 | Olden et al. |

* cited by examiner

*Primary Examiner* — Christopher L Templeton
(74) *Attorney, Agent, or Firm* — Coats & Bennett PLLC

(57) ABSTRACT

A medical instrument and procedure for removing a food mass lodged in the esophagus of a patient. First, the food mass is magnetized. Thereafter, a medical instrument that includes a magnetic retriever is inserted into an endoscope, for example, into the esophagus. The magnetic retriever includes a magnet that applies a drawing force to the lodged magnetized food mass, causing the magnetized food mass to become dislodged. Once dislodged, the food mass is retrieved and removed from the esophagus.

9 Claims, 4 Drawing Sheets

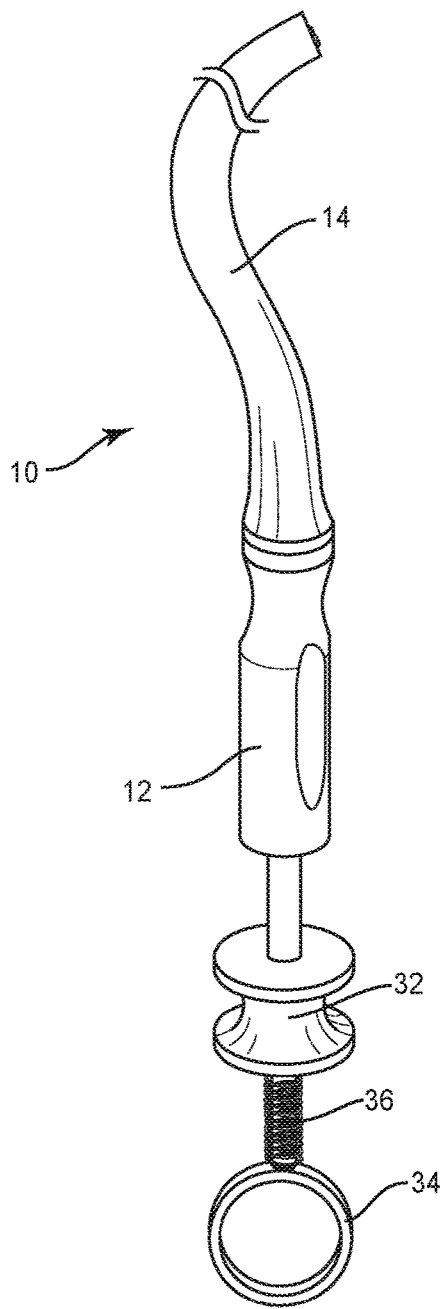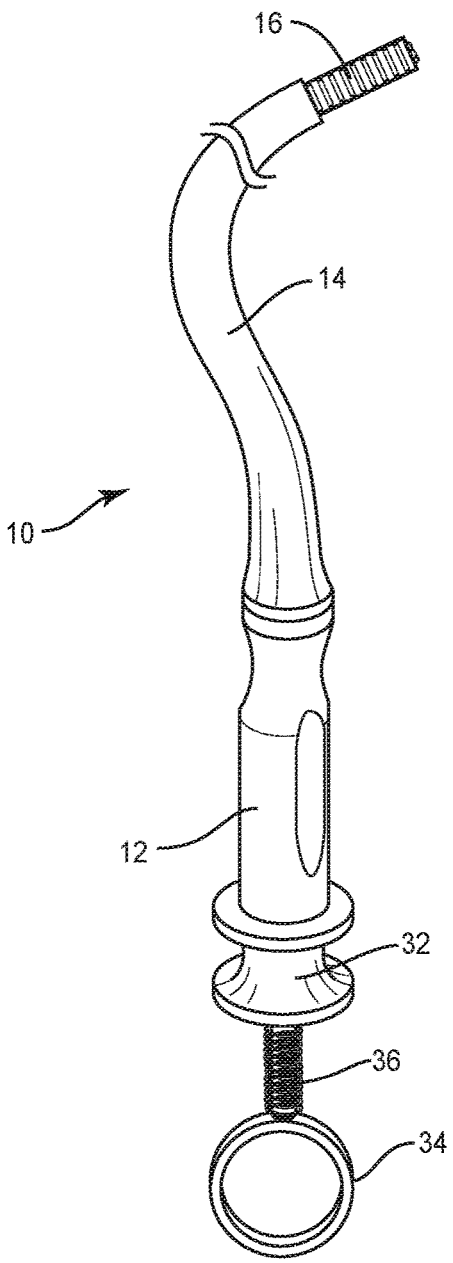
FIG. 1
FIG. 2

PROCEDURE FOR REMOVING A FOOD MASS LODGED IN THE ESOPHAGUS

FIELD OF THE INVENTION

The present invention relates to medical instruments and medical procedures, and more particularly to a medical instrument and a medical procedure designed to remove a food mass lodged in the esophagus of a person.

BACKGROUND

One of the more common occurrences in emergency rooms at hospitals is the presence of a patient with a mass of food, typically meat, lodged in the esophagus. Removing these lodged food particles or food masses is often problematic. That is, removing food masses lodged in the esophagus is often tedious and time consuming, especially when the food that is lodged in the esophagus is a small piece of meat. One approach to dislodging the food mass is to engage the food mass with an instrument and break the food mass into small particles, effectively reducing the size of the lodged mass of food which, when successful, dislodges the food mass. As noted above, this is not always easy and can in some cases take hours to successfully dislodge the food mass.

Therefore, there has been and continues to be a need for a medical instrument and procedure that enables a doctor to quickly and easily dislodge a food mass, particularly a food mass, such as a piece of meat, from the esophagus.

SUMMARY OF THE INVENTION

The present invention relates to a medical instrument and a medical procedure for removing a food mass lodged in the esophagus of a patient. First, the food mass is magnetized. Then a magnetic retriever is inserted into the esophagus. The magnetic retriever includes a magnet that effectively applies a drawing force to the magnetized food mass, causing it to become dislodged. Once dislodged, the food mass is retrieved and removed from the esophagus.

In one particular embodiment, the medical instrument includes a basket and an associated magnet. In an operative position, the basket is open and placed adjacent the lodged magnetized food mass. The presence of the magnet in close proximity to the magnetized food mass induces the food mass towards the open basket. Once dislodged by the force of the magnet, the food mass is retrieved by causing the dislodged food mass to enter the open basket. Thereafter, the basket and the dislodged food mass are removed from the patient.

Other objects and advantages of the present invention will become apparent and obvious from a study of the following description and the accompanying drawings which are merely illustrative of such invention.

BRIEF DESCRIPTION OF THE DRAWINGS

FIG. 1 is a perspective view of the medical instrument of the present invention shown in the inoperative position.

FIG. 2 is a perspective view of the medical instrument shown with an inner housing being projected from the distal end.

DESCRIPTION OF THE INVENTION

Figures 3, 4:
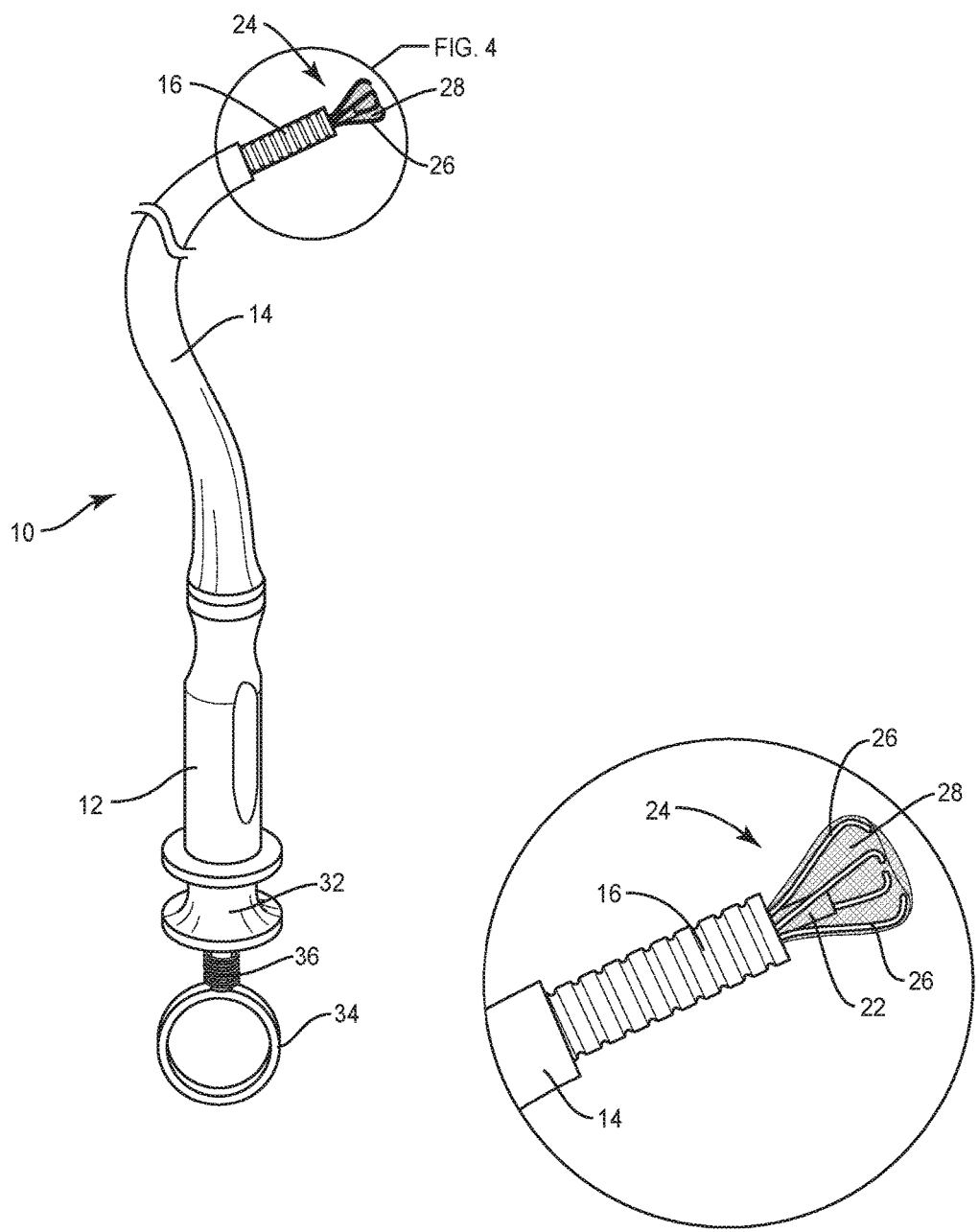
FIG. 3 is a perspective view showing the medical instrument in the operative position.
FIG. 4 is an enlarged view of the distal end of the medical instrument shown in FIG. 3.

As alluded to above, the present invention presents a medical procedure for removing a food mass lodged in a patient's esophagus. The basic procedure entails four steps. First, the lodged food mass is magnetized. It is sufficiently magnetized such that the food mass, as a whole, will respond to a magnet placed next to or relatively close to the lodged food mass. The second step entails dislodging the food mass. This is achieved by utilizing a magnet. A magnet is inserted into the esophagus and brought in close proximity to the lodged food mass. The presence of the magnet exerts a magnetic force on the lodged magnetized food mass. This magnetic force induces the lodged food mass to move towards the magnet, resulting in the food mass being dislodged. Once the food mass is dislodged, it is captured. Various ways can be employed to capture the dislodged food mass. In one embodiment, this is achieved by a retriever (e.g. a basket) that receives the dislodged food mass. Once in the retriever or other holding structure, the dislodged food mass is removed from the esophagus and from the body of the patient.

There are various ways to magnetize the food mass while lodged in the esophagus. Fundamentally, the lodged food mass is impregnated with a material that is attracted to the magnet. One common material that can be used to magnetize the lodged food mass is iron. Iron can be utilized in various forms. For example, iron powder or iron fines or small iron particles can be utilized. In addition, it is hypothesized that an iron solution might be used to impregnate the lodged food particle. In one example, the magnetizing process may entail the use of iron fines or small particles that are injected or otherwise inserted into the lodged food mass. This would be carried out under the direction of a physician and would entail delivering the magnetizing material through the mouth of the patient and down into the esophagus and to the lodged food mass. Various known medical instruments can be utilized to carry the magnetizing material to the site where the lodged food mass lies. With the use of a fluoroscope, the physician can deliver the magnetizing material into the lodged food mass in order to cause the food mass to have magnetic qualities such that the lodged food mass is attracted to a magnet.

Turning to the drawings, a medical instrument is shown therein and indicated generally by the numeral 10. Medical instrument 10 is designed to be used in conjunction with a conventional endoscope and to dislodge the food mass 40, capture the dislodged food mass, and remove the dislodged food mass from the body of the patient. See FIG. 5. Viewing medical instrument 10 in more detail, the same includes a handle 12 and an outer sheath 14 extending from the handle. In the embodiment shown herein, the handle and outer sheath 14 form an integral unit. It is understood and appreciated, however, that the handle 12 and sheath 14 may comprise two separate components in the medical instrument 10. The outer sheath 14 is constructed of a soft rubber or plastic material that is flexible and pliable such that it can be inserted into the side port of an endoscope and directed through the endoscope in a conventional manner. See FIG. 5. Outer sheath 14 includes a central opening that aligns with an opening in the handle 12. A pliable housing 16 extends through the handle 12 and through the outer sheath 14. Housing 16, as discussed below, can be articulated or moved back and forth in the outer sheath 14. An actuator 18 extends through an opening in the housing 16. Actuator 18, which in one embodiment is a cable, can be moved back and forth to actuate a retriever indicated generally by the numeral 24. The retriever 24, as well as a magnet 22, is secured to the distal end of the actuator 18. Retriever 24 is designed to capture and remove the dislodged food mass. Various retriever designs can be utilized. In the example shown in the drawings, the retriever 24 assumes the form of a basket. As shown in the drawings, the basket comprises an open frame with netting 28 secured about the frame to form the basket. In the exemplary design in the drawings, the frame of the basket is formed by a series of tines 26. The tines 26 are secured to the distal end of the actuator or cable 18 and form the framework for supporting the netting 28. Tines 26 can be constructed of various materials. In one example, the tines are constructed of spring steel or spring plastic which enables the tines to be collapsed in the housing 16 and to spring open to form the basket when the retriever is projected from the distal end of the housing 16.

The basket assumes two basic positions, a retracted inoperative position and an open operative position. As will be discussed later, in the retracted inoperative position (FIG. 1), the basket is collapsed and contained within the housing 16 of the medical instrument 10. In the operative open position (FIG. 3), the basket projects from the distal end of the medical instrument 10 and assumes an open configuration. That is, in the operative position, the basket includes an open top through which the dislodged food mass may pass.

As seen in the drawings, the tines 26 are slightly curved at the top or outer ends. Tines 26 as a group close and open. That is, when the basket assumes the closed inoperative position, the tines 18 are collapsed as a group. When the basket assumes the open operative position, the tines 26 assume the open configuration shown win FIG. 4. Thus, the tines have a spring quality and are configured and incorporated into the medical instrument 10 such that they are biased towards the open position shown in FIG. 4. That is, when the tines 26 are extended from the housing 16, the individual tines 26 as a group spring open to the open position shown in FIG. 4. As noted above, the basket includes a netting 28 and the netting is secured to the tines. Thus, the tines, along with the netting, form the basket that will receive and hold the dislodged food mass when the medical instrument 10 is used in a procedure for removing the food mass.

Medical instrument 10 includes a magnet 22. Generally, the magnet 22 is also disposed on the distal end of the medical instrument 10. Magnet 22 can be incorporated and disposed in various ways. In the embodiment illustrated in the drawings (FIG. 4), the magnet 22 is incorporated into the basket. Magnet 22, or at least a portion thereof, projects into the bottom center portion of the basket.

In the embodiment illustrated herein, the actuator 18 is a cable. The cable is sufficiently flexible to bend and curve as it moves through the housing 16. However, the cable 18 is sufficiently rigid in the direction of its longitudinal axes in order that it can be pushed and pulled through the housing by the control mechanisms described below.

Medical instrument 10 includes a control mechanism disposed below the handle 12 for actuating the housing 16 and the actuator or cable 18. In particular, the control mechanism includes a finger slide 32 that is attached to an end portion of the housing 16. By moving the finger slide 32 up and down, as viewed in FIGS. 6-7, the housing 16 is moved back and forth within the outer sheath 14 and the handle 12. When the housing 16 is fully extended from the distal end of the medical instrument, the finger slide 32 abuts against the bottom of the handle 12, preventing the housing 16 from being further extended.

Figures 6, 7, 8:
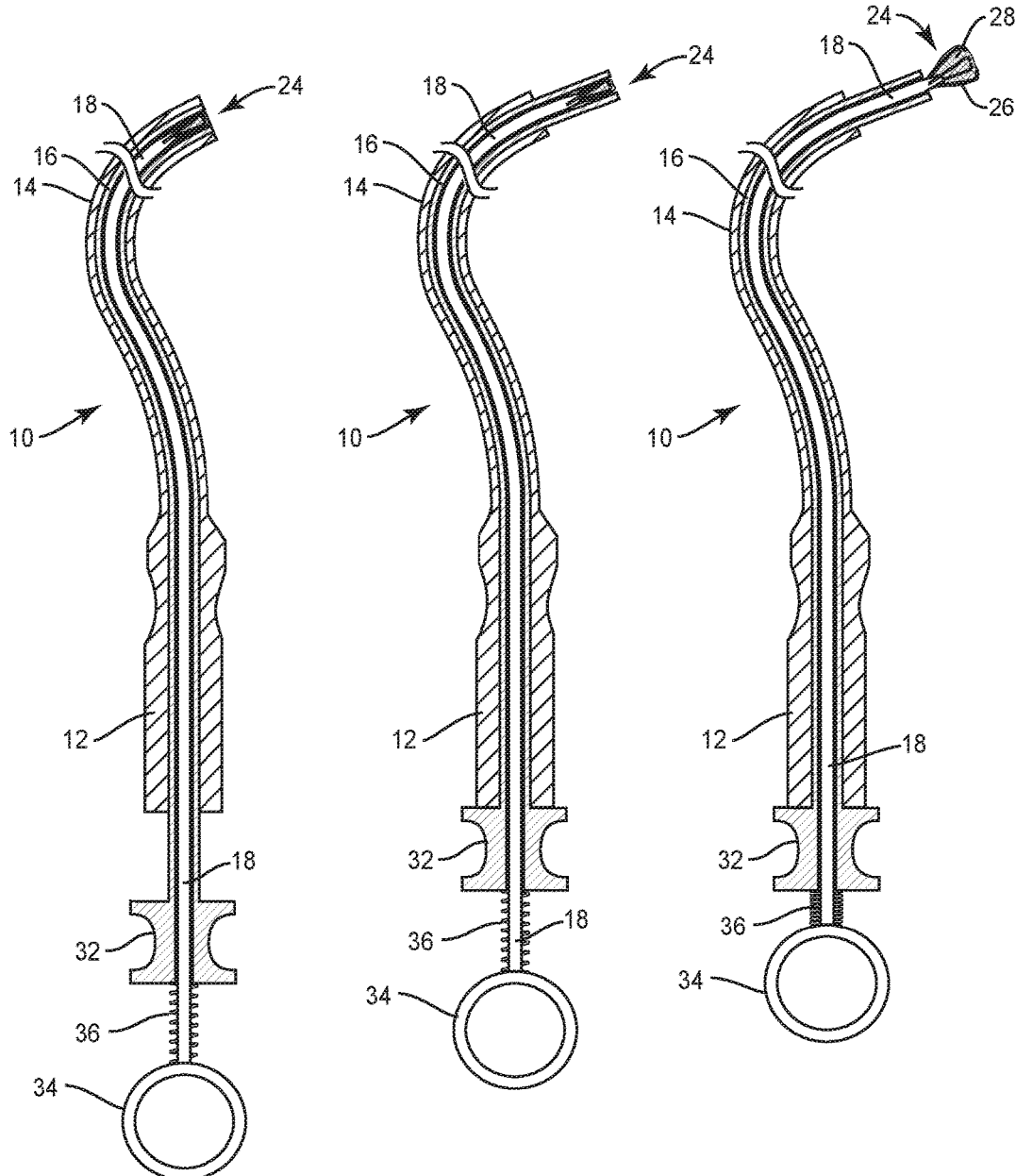
FIG. 6 is a cross-sectional view of the medical instrument shown in the inoperative position.
FIG. 7 is a cross-sectional view of the medical instrument illustrating the projection of the inner housing from the distal end of the medical instrument.
FIG. 8 is a cross-sectional view of a medical instrument in the operative position.

Finger slide 32 also includes an axial opening for accepting and receiving the actuator or cable 18. The actuator cable 18 is free to slide through the central opening in the finger slide 32. As seen in FIGS. 6-7, the actuator or cable 18 extends downwardly through the finger slide 32 and connects to a thumb ring 34. A spring 36 is interposed between the bottom of the finger slide 32 and the ring 34. Spring 36 tends to bias the actuator or cable 18 towards a retracted position which is shown in FIGS. 1 and 6. The spring 36 and basket can be specified and designed such that the spring has just enough force to pull the retriever 24 back into the housing 16.

Figure 5:
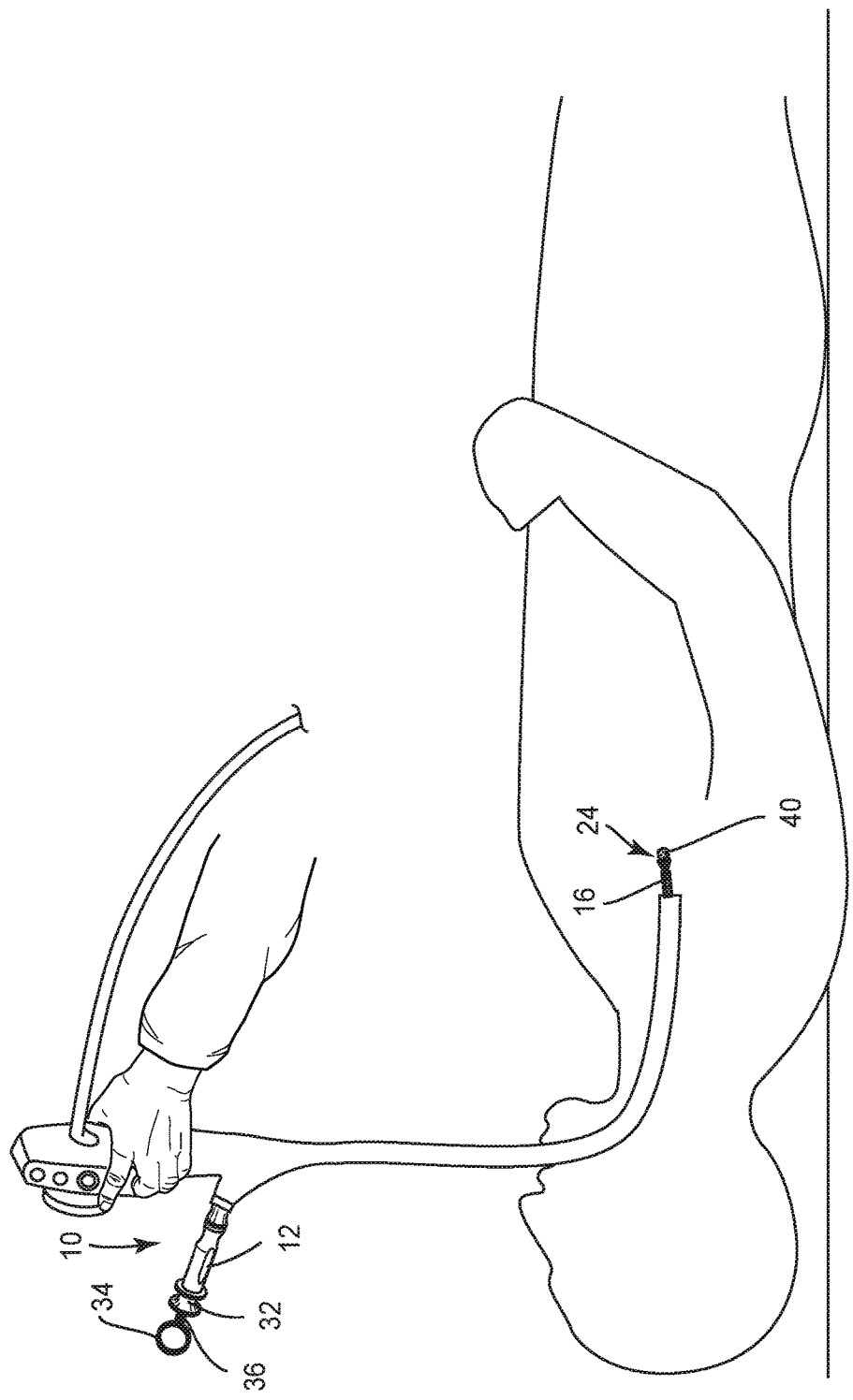
FIG. 5 is a view showing the medical instrument of the present invention employed in an endoscope and directed towards a lodged food mass in the endoscope of the patient.

In order to utilize the medical instrument 10 and perform the procedure described herein for dislodging and removing a mass of food lodged in the esophagus of a patient, the medical instrument is employed in a conventional endoscope. That is, the medical instrument of the present invention is directed into and through a side port of the endoscope as viewed in FIG. 5. Details of the endoscope are not presented herein because they are not per se material to the present invention and endoscopes are well known and appreciated by those skilled in the art. A mouth block may be used to keep the mouth of the patient open. In any event, the insertion of the medical instrument 10 is preceded by a procedure for magnetizing the lodged food mass which is discussed above. After the food mass has been magnetized, the medical instrument is inserted into the endoscope with the housing 16 being fully retracted and with the retriever or basket 24 retracted into the distal end portion of the housing. This is shown in FIGS. 1 and 6. The distal end of the outer sheath 14, with the aid of a fluoroscope for example, is manipulated into the esophagus and eventually disposed upstream of the lodged food mass 40. The distal end of the outer sheath 14 is held slightly above the lodged food mass 40 such that there is a space between the distal end of the outer sheath 14 and the lodged food mass. At this point, the finger slide 32 and thumb ring 34 are disposed in the positions shown in FIG. 6. Now the housing 16 is extended from the outer sheath 14 as shown in FIGS. 5 and 7. The terminal end of the housing 16 is brought into close proximity with the lodged food mass as shown in FIG. 5. At this point, the retriever 24 is extended from the terminal end of the housing 16. This is accomplished by pushing the thumb ring 34 towards the finger guide 32 and compressing the spring 36 in the process. See FIG. 8. This causes the basket and the tines 26 and netting 28 thereof to spring open and form the basket shown in FIG. 4. Note that the basket includes an open end that faces the lodged food mass. The basket can be manipulated relatively close to the lodged food mass. Note in FIG. 4 where the magnet 22 is disposed in the basket or at least projects partly into the basket. Thus, in this position the magnet 22 is relatively close to the magnetized lodged food mass. The presence of the magnet 22 exerts a magnetic force on the magnetized lodged food mass and causes the food mass to be drawn towards the magnet, dislodging the food mass in the process. Now the open basket can be manipulated around the dislodged food mass and held in the basket. In some cases, the magnet 22 may alone be effective to induce the dislodged magnetic food mass through the opening in the basket and into the interior of the basket.

At this point, the basket 26 can be closed or slightly closed around the food mass held therein by manipulating the thumb ring 34. In some cases, the medical instrument 10 can be withdrawn from the patient without fully retracting the basket into the housing 16. As in some cases, the food mass held in the basket may be so large that it might be difficult to retract the basket into the terminal end of the housing. However, in other cases, once the food mass is in the basket, the basket can be collapsed and closed and retracted into the housing 16, retaining the dislodged food mass in the process. Now the medical instrument can be removed from the patient.

As the specification and drawings describe, the present invention, in the form of a medical instrument, makes it relatively easy to dislodge a food mass caught in the esophagus of a patient. By magnetizing and using a magnet to dislodge the food mass, the process can be carried out quickly and easily without requiring tedious and time-consuming attempts to break the lodged food mass apart so that it can be removed from the esophagus.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of removing a lodged food mass from the esophagus of a person comprising:
    magnetizing the food mass while the food mass is lodged in the esophagus;
    then directing a retriever into the esophagus of the person and towards the lodged food mass and wherein the retriever includes a magnet and a holder;
    positioning the magnet of the retriever in close proximity to the lodged food mass;
    utilizing the magnet to dislodge the magnetized food mass; and
    capturing the dislodged magnetized food mass with the holder and removing the captured food mass from the person.

2. The method of claim 1 wherein magnetizing the food mass includes injecting magnetic particles or fines into the food mass while the food mass is lodged in the esophagus.

3. The method of claim 1 wherein the holder includes a collapsible basket that assumes operative and non-operative positions and wherein in the non-operative position the collapsible basket assumes a collapsed position in a housing and wherein in the operative position the basket projects from the housing and assumes an open position.

4. The method of claim 3 wherein the magnet lies at least partially in the basket when the basket assumes the operative position and wherein the method includes pushing the open basket and magnet towards the lodged food mass and aligning an opening in the basket with the lodged food mass wherein the magnet tends to draw the lodged food mass into the open basket.

5. The method of claim 3 wherein the food mass is captured in the basket, wherein after the food mass is captured in the basket, the method includes collapsing the basket and withdrawing the basket into the housing and removing the housing from the person.

6. The method of claim 1 wherein the holder includes a collapsible basket formed by a series of tines and a netting connected to the tines; and wherein the tines are flexible and are moved between a collapsed position where at least a portion of the tines are contained within a housing and an expanded position where the tines project from the housing and together with the netting form the collapsible basket.

7. The method of claim 6 wherein the magnet is at least partially disposed in the basket when the basket projects from the housing and assumes an operative position.

8. The method of claim 1 wherein the retriever is directed through an endoscope that is positioned in the esophagus of the person.

9. The method of claim 1 wherein the retriever is directed through a port associated with an endoscope and directed through the endoscope to a terminal end of the endoscope where the retriever is projected out of the terminal end of the endoscope towards the lodged food mass.

* * * * *